United States Patent [19]

Butcher

[11] Patent Number: 5,403,919
[45] Date of Patent: Apr. 4, 1995

[54] METHOD TO CONTROL LEUKOCYTE EXTRAVASATION

[75] Inventor: Eugene C. Butcher, Portola Valley, Calif.

[73] Assignee: Board of Trustees of the Leland Stanford Junior University Stanford University, Stanford, Calif.

[21] Appl. No.: 34,791

[22] Filed: Mar. 3, 1993

Related U.S. Application Data

[63] Continuation of Ser. No. 717,030, Jun. 18, 1991, which is a continuation of Ser. No. 84,490, Aug. 11, 1987, abandoned.

[51] Int. Cl.$^6$ .................... A61K 39/395; C07K 15/28
[52] U.S. Cl. ........................ 530/388.22; 424/130.1; 424/143.1; 424/152.1; 530/388.25; 530/808; 530/868
[58] Field of Search ............ 530/388.22, 388.85, 530/389.1, 388.25, 808, 868; 424/85.8, 130.1, 143.1, 152.1

[56] References Cited

FOREIGN PATENT DOCUMENTS 0061141 9/1982 European Pat. Off. ........ C07G 7/00

OTHER PUBLICATIONS

Paul, W. F. (ed.) *Fundamental Immunology*, 3rd edition (1993) pp. 145, 179–184 only.
Rothlein, R. et al., J. Immunology, 137:1270–1274 (Aug. 15, 1986), "A human intercellular adhesion molecule (DAM-1) distinct from LFA-1".
E. C. Butcher, 1986 Curr. Topics in Microbiol. and Immunol. pp. 85–121.
E. C. Butcher, et al. 1979 J. Immunol. 123(5):1996–2003, Lymphocyte adherence.
Butcher, E. C., et al., J. Cellular Biochemistry 30:121–131 (1986), "Interactions between endothelial cells and leukocytes".
Duijvestijn, A. M., et al., J. Immunology 138:713–719 (Feb., 1987), "Lymphoid tissue- and inflammation-specific endothelial cell differentiation defined by monoclonal antibodies".
Proc. Natl. Acad. Sci. USA 83:9114–9118 (Dec., 1986), "Interferon-gamma regulates an antigen specific for endothelial cells involved in lymphocyte traffic".
Gallatin, W. M., et al., Nature 304:30–34 (Jul. 1983), "A cell-surface molecule involved in organ-specific homing of lymphocytes".
J. Cell Biology 105:983–990 (1987), "Lymphocyte recognition of high endothelium: antibodies to distinct epitopes of an 85–95 glycoprotein antigen differentially inhibit lymphocyte binding to lymph node, mucosal, or synovial cells".
Jalkanen, S., et al., Science 233:556–558 (1 Aug. 1986), "A distinct endothelial cell recognition system that controls lymphocyte traffic into inflamed synovium".
Lewinsohn, D. M., et al., J. Immunology 138:4313–4321 (Jun. 15, 1987), "Leukocyte-endothelial cell recognition evidence of a common moelcular mechanisms shared by neutrophils, lymphocytes and other leukocytes".
Wallis, W. J., et al., J. Immunology 135(4):2323–2330 (Oct., 1985), "Human monocyte adherence to cultured vascular endothelium: monoclonal antibody-defined mechanisms".
Yednock, T. A., et al., J. Cell Biology 104:725–731 (Mar., 1987), "Receptors involved in lymphocyte homing: relationship between a carbohydrate-binding receptor and the MEL-14 antigen".
Jalkanen et al., *Chemical Abstracts*, 107:533, Abstract No. 173820y, (1987). *J. Cell Biol.*, 105(2):983–990, Title: Lymphocyte recognition of high endothelium: antibodies to distinct epitopes of an 85–95-kD glyocoprotein antigen differentially inhibit lymphocyte binding to Lymph node, mucosal, or synovial endothelial cells.
Jalkanen et al., *Biological Abstracts*, 83:, Abstract No. 34111, (1987), *Eur. J. Immunol*, 16(10):1195–1202 (1986). Title: A lymphoid cell surface glycoprotein involved in endothelial cell recognition and lymphocyte homing in man.
Jalkanen et al., *Biological Abstracts*, 33, Abstract No. 33106700, (1987). *Cell Differentiation*, 20:120S (1987). Title: An 85–95KDA clycoprotein class is involved in organ-specific homing of human lymphocytes.
Jalkanen et al., *Science*, 233:556–558 (Aug. 1986). Title: A distinct endothelial cell recognition system that controls lymphocyte traffic into inflamed synovium.

*Primary Examiner*—Christine M. Nucker
*Assistant Examiner*—Thomas Cunningham
*Attorney, Agent, or Firm*—Bertram I. Rowland

[57] ABSTRACT

Novel antibodies that recognize endothelial cell surface molecules and block leukocyte extravasation are provided. These antibodies recognize tissue-specific endothelial cell surface molecules and block lymphocyte migration from the blood into tissues such as mucosal lymphoid organs and peripheral lymph nodes. Novel endothelial cell surface proteins involved in leukocyte extravasation and having a molecular weight of approximately 58,000 to 69,000 daltons and express a tissue-specific determinant are also described. The antibodies are used in an immunotherapeutic method to treat individuals having a disease or inflammation-associated pathology in which leukocyte extravasation plays a role.

7 Claims, No Drawings

METHOD TO CONTROL LEUKOCYTE EXTRAVASATION

Reference to Government Grant

The United States Government has rights to this invention pursuant to Grant No. GM-37734, awarded by the National Institutes of Health.

This is a continuation of application Ser. No. 07/717,030, filed Jun. 18, 1991, which was a continuation of application Ser. No. 07/084,490, filed Aug. 11, 1987, now abandoned.

DESCRIPTION

1. Technical Field

The invention is in the fields of immunotherapy and immunodiagnostics. More specifically, it relates to controlling leukocyte extravasation into particular sites in the body by using antibodies to interfere with the function of specific endothelial cell ligands or molecules involved in site-specific leukocyte adhesion to endothelial cells.

2. Background Art

Most mature lymphocytes continuously circulate between the various lymphoid organs and other tissues of the body, traveling via the lymph and bloodstream. These lymphocytes are said to recirculate because they move from the bloodstream into lymphoid organs, then to the collecting efferent lymphatics, and eventually back to the bloodstream where they reenter the cycle. Although the pace of recirculation is a function of lymphocyte class and stage of differentiation, the average lymphocyte completes this recirculatory cycle, and thus finds itself in a new lymphoid organ or tissue, roughly every 1-2 days. This cellular shuffling allows the full repertoire of lymphocyte specificities to be available for immune reaction throughout the body and probably also facilitates the cell-cell interactions required for the generation and control of immune responses.

Essential to this process of recirculation is the ability of migrating lymphocytes to leave the blood at appropriate sites. Lymphocytes have the remarkable capacity to recognize and bind selectively to specialized endothelial cells in lymphoid organs and sites of inflammation, binding initially to the luminal surface and then migrating through the vessel wall into the surrounding tissues. Outside of the spleen, most such migration occurs through the postcapillary venules in lymph nodes and Peyer's patches. These vessels are characterized by distinctive plump endothelial cells and thus are referred to as "high endothelial venules," or HEV. The interaction of lymphocytes with HEV is of central importance in controlling lymphocyte traffic and has been studied extensively using an in vitro model, first developed by Stamper and Woodruff (1976) *J Exp Med* 144:828-833, in which viable lymphocytes recognize and bind to HEV in frozen sections of murine or human (Jalkanen and Butcher (1985) *Blood* 66:577-582) lymph nodes or mucosal lymphoid organs (Butcher, E. C. (1986) *Curr Top Microbiol Immunol* 128:85-122). The in vitro binding of lymphocyte populations to HEV in frozen sections accurately reflects their capacity to adhere to HEV under physiologic conditions (Butcher et al. (1979) *J Immunol* 123:1996).

Until now, studies in lymphocyte trafficking were directed at identifying cell surface antigens on lymphocytes as demonstrated in studies concerning "homing receptors" involved in lymphocyte recognition of HEV. For example, MEL-14, a rat monoclonal antibody that selectively blocks mouse lymphocyte binding to peripheral lymph node HEV, appears to define lymphocyte surface receptors mediating specific recognition of peripheral lymph node HEV (Gallatin et al. (1983) *Nature* 304:30-34). Jalkanen et al. [(1986) *Eur J Immunol* 16:1195-1202] described a rat monoclonal antibody, Hermes-1, that defines 85-95 kilodalton (kD) human lymphocyte surface glycoproteins involved in lymphocyte binding to lymph node HEV. They showed further (*J Cell Biol*, in press) that this same class of molecules defined by Hermes-1 included members involved in controlling lymphocyte-endothelial cell interaction and lymphocyte homing to mucosal lymphoid (appendix, Peyer's patches) and to inflamed synovial tissues in rheumatoid arthritis and Lyme disease arthritis. Hermes-1 defines related 85-95 kD glycoproteins on cells capable of binding to lymph node, mucosal, and synovial HEV. MEL-14, the monoclonal antibody against mouse lymphocyte homing receptors for lymph node HEV, cross reacts with human lymphocyte Hermes-1 antigen, and specifically blocks human lymphocyte binding to lymph node HEV. Monoclonal antibody Hermes-3, which defines a distinct epitope on the Hermes-1 antigen, specifically blocks human lymphocyte binding to mucosal (appendix, Peyer's patch) lymphoid HEV. Finally, a polyclonal antiserum against the Hermes-1 antigen blocks lymphocyte binding to all known HEV classes: lymph node, mucosal, synovial, and skin (Butcher, E. C., *Curr Top Microbiol Immunol*, supra). Thus lymphocytes use a family of closely related receptors to extravasate from the blood into different lymphoid organs and tissues of the body.

It has been recently shown that this family of molecules, defined by MEL-14 in the mouse and Hermes-1 and Hermes-3 in the human, is expressed not only by lymphocytes, but also by neutrophils, monocytes, eosinophils, large granular lymphocytes, natural killer cells, and other leukocytes: all of these leukocytes stain intensely with MEL-14 in the mouse and with Hermes-1 in the human. The neutrophil MEL-14 antigen is similar to the MEL-14-defined lymphocyte homing receptor, migrating in SDS-PAGE with an apparent molecular weight of roughly 100 kD (within the range of molecular weights exhibited by the MEL-14 antigen on mouse lymphoid cell lines), and displaying an acidic pI of 4.2, identical to that of the lymphocyte antigen. Furthermore, it has been shown that neutrophils and monocytes use these molecules to interact with tissue-specific endothelial cell determinants (Lewinsohn et al. (1987) *J Immunol* 138: 4313-4321). Thus not only lymphocytes, but neutrophils, monocytes and probably all leukocytes employ related or identical surface recognition elements for tissue-specific endothelial cell determinants. This family of receptors is central in permitting access of all leukocytes to tissues and organs from the blood.

It has also been determined that antibodies against these leukocyte receptors inhibit leukocyte interactions with tissue-specific endothelial cells not only in vitro, but also in vivo. For example, MEL-14 inhibits the entry of both lymphocytes (Gallatin et al., supra) and neutrophils (Lewinsohn et al., supra) into peripheral lymph nodes or sites of inflammation.

Inflammatory reactions are a common cause of tissue pathology in human and animal disease. This is particularly clear in the autoimmune diseases, in which human and animal immune systems respond inappropriately to one or more organs or tissue elements of the body. However, inflammatory responses also cause clinical problems in many other diseases. Normal inflammatory and immune responses, while important in providing protection from exogenous infectious insults, often have deleterious pathologic effects. As an example, immune responses to tuberculosis and leprosy often result in tissue damage worse than that induced directly by the responsible bacterial agents. Secondary effects of inflammation or immune responses, such as immune complex deposition, vasculitis, and local allergic phenomena, such as diarrhea in gluten enteropathy or bronchospasm in asthmatic allergies, can also be clinically important or even life threatening. Immune responses and inflammation are also life threatening to organ transplant patients; the normal host immune response to the transplanted organ is the most common cause of transplant failure.

The ability to control inflammatory and immune processes is thus central to the therapy of a wide spectrum of diseases. General immunosuppressive agents acting to suppress or regulate the immune system throughout the body (e.g., corticosteroids, aspirin) are widely employed in this context and illustrate the importance of the immunosuppressive approach in clinical patient care. With the exception of topical therapy for external inflammatory diseases (e.g., in the skin) these agents are given parenterally, and therefore cause suppression of desirable immune responses in organs or tissues not involved in the disease process being targeted. Therefore, and particularly in the context of inflammatory or autoimmune diseases clinically manifested by selective organ or tissue pathology, it would be preferable to have a means of suppressing immune responses in a more selective, tissue-specific manner.

The tissue-specific endothelial cell ligands of the present invention are centrally positioned to control the inflammatory process in tissues by regulating the access of diverse inflammatory cells. The ability to manipulate the leukocyte and endothelial cell molecules involved—e.g., to block their function with monoclonal antibodies—offers novel approaches to clinical problems of local destructive immune and inflammatory reactions.

Disclosure of the Invention

The present invention provides monoclonal antibodies having recognition for tissue-specific endothelial cell surface antigens, which inhibit the binding of leukocytes to the endothelial cells and thereby inhibit lymphocyte extravasation via such endothelial cells in vivo. These antibodies recognize endothelial cell surface antigens derived from differentiated tissues of the body including peripheral lymph nodes and mucosal lymphoid tissues. Hybridoma cell lines secreting these monoclonal antibodies are also provided.

Another aspect of the invention discloses a purified endothelial cell surface protein which has:

(a) a molecular weight of approximately 58,000–69,000 daltons in reduced form as determined by sodium dodecyl sulfate-polyacrylamide gel electrophoresis (SDS-PAGE); and (b) expresses an antigenic determinant which binds an antibody forming a complex which blocks lymphocyte homing in vivo, said protein being substantially free of other proteins.

Yet another aspect of the invention is an immunotherapeutic method for the treatment of an individual to control a disease associated with leukocyte extravasation. This method comprises administering an amount of an antibody effective to block leukocyte extravasation in that individual.

Another aspect of the invention is to provide a method to diagnose the presence of disease or predisposition of an individual to manifest such disease using the particular antibodies of the invention.

MODES FOR CARRYING OUT THE INVENTION

The practice of the present invention will employ, unless otherwise indicated, conventional techniques of molecular biology, microbiology, recombinant DNA, and immunology, which are within the skill of the art. Such techniques are explained fully in the literature. See, e.g., Maniatis, Fritsch and Sambrook, MOLECULAR CLONING: A LABORATORY MANUAL (1982); ANIMAL CELL CULTURE (R. K. Freshney, ed. 1986); IMMOBILIZED CELLS AND ENZYMES (IRL Press, 1986); B. Perbal, A PRACTICAL GUIDE TO MOLECULAR CLONING 91984); and HANDBOOK OF EXPERIMENTAL IMMUNOLOGY, Volumes I–IV (D. M. Weir and C. C. Blackwell, eds., 1986, Blackwell Scientific Publications).

In describing the present invention, the following terminology will be used in accordance with the definitions set forth below.

"Antibody" refers to a member of a family of glycosylated proteins called immunoglobulins, which can specifically combine with an antigen. The term is intended to include all classes of immunoglobulins (IgG, IgM, IgA, IgD, or IgE) and antigen binding fragments (e.g., Fab, F(ab')$_2$, Fab', Fv) as well as whole immunoglobulins.

"Antigen" refers to a protein or synthetic peptide compound which will produce antibody formation without chemical modification. More particularly, the term refers to an endothelial cell surface molecule or ligand.

"Derivative" is intended to include any modification of the native or reduced 58,000–69,000 dalton (58–69 kD) protein that retains the antibody binding or functional leukocyte binding activity of the native 58–69 kD protein. The term is intended to include, without limitation, fragments, oligomers or complexes of the protein, polypeptides or fusion proteins made by recombinant DNA techniques whose amino acid sequences are in whole or part identical or substantially identical (e.g., differ in a manner that does not affect antibody binding adversely) to those of the 58–69 kD protein or that of an active fragment thereof, or that have different substituents (e.g., lack of glycosylation, altered glycosylation), and conjugates of the proteins or such fragments, oligomers, polypeptides and fusion proteins and carrier proteins.

"Functional equivalent" means an antibody that recognizes the same antigens as antibody MECA-367 or MECA-79, respectively and blocks leukocyte-endothelial cell interactions. It is intended to include antibodies of murine or other origin of the same or different immunoglobulin class, and antigen binding fragments of MECA-367, MECA-79 and other such antibodies.

According to the invention, antibodies are provided which identify and isolate tissue-specific endothelial cell surface molecules involved in the extravasation and homing of lymphocytes and other leukocytes into particular organs or tissues of the body, or into tissue sites representing particular states of tissue (e.g., inflammation). These antibodies identify endothelial cell surface molecules mediating recognition of migrating lymphocytes and other leukocytes. Moreover, the antibodies described herein discriminate between endothelial cells in different organs, tissues, or tissue states of the body. Such organ-specific interactions define endothelial cell determinants of HEV in peripheral lymph nodes (e.g., cervical, axillary, brachial, inguinal, popliteal), in mucosa-associated lymphoid tissues (e.g., Peyer's patches, appendix), in inflamed synovium, as well as define other tissue-specific endothelial cell determinants believed to exist in other organs including lung, brain, liver, kidney, ovaries, uterus, pancreas, heart, skin or particular skin sites, eyes, etc.

Following the methodology described herein, a wide variety of antibodies which recognize and functionally interfere with endothelial cell molecules involved in the extravasation and homing of lymphocytes and other leukocytes can be constructed.

The general procedure for making monoclonal antibodies by hybridoma technology is well known. Monoclonal antibodies directed against endothelial cell surface receptors may be made from antibody-secreting hybridomas by such procedures as those described by Kohler and Milstein (1975), *Nature* 356:497; and Levy and Dilley (1978), *Proc Natl Acad Sci USA*, 75:4211. Briefly, these processes involve fusing myeloma cells and lymphocytes by using a fusogen, typically polyethylene glycol. Myeloma cell lines that may be used in the process are known and available. The lymphocytes, typically either spleen cells or B cells, are obtained from mice or rats immunized with crude stromal preparations of particular organs or tissues, or states of tissue (e.g., lymph node stroma, synovial stroma, or stroma of any other lymphoid or inflamed tissue) or with isolated endothelial cells from such tissues. The fused cells or hybridomas are then expanded in a nutrient medium containing hypoxanthine, aminopterin, and thymidine (HAT). The cells surviving the incubation are assayed for production of the desired antibody and positive cells are sorted and cloned by known techniques. Following production of hybridomas, supernatants are screened for relevant antibodies: 1) by immunohistology, seeking antibodies defining antigenic determinants expressed in a tissue-specific manner on vessels involved in leukocyte traffic (e.g., antibodies staining synovial HEV more intensely than HEV in other sites); 2) in a functional in vitro assay of antibody blocking of leukocyte interactions with positive vessels; and 3) in animal models by testing the ability of intraveneously injected antibody to inhibit organ-specific lymphocyte or leukocyte extravasation. The monoclonal antibodies expressed by the clones may be harvested and purified by known techniques.

Although xenogeneic antibodies may be used in the invention, one could also use allogeneic or hybrid antibodies to reduce the likelihood of the antibodies themselves inducing an immune response from the host. An allogeneic monoclonal antibody is one that is expressed by a hybridoma made by fusing cells from the same animal species as the host. Hybrid monoclonal antibodies can be genetically engineered using human constant regions and mouse or rat variable regions as described by Morrison et al (1984) *Proc Natl Acad Sci USA* 81:6851–5. The antibodies may be from one or more immunoglobulin classes (IgM, IgG, IgA, IgD, or IgE) depending upon the particular disease and individual involved.

The endothelial cell surface molecules described herein are believed to comprise a family of antigenically and structurally related endothelial cell surface molecules which mediate the recognition of migrating lymphocytes. As described in the Background Art, lymphocyte recognition of endothelial cells in different tissues involves a family of closely related but functionally distinct lymphocyte surface receptors (the gp85–95 kD defined by Hermes-1) that interact with a complementary family of closely related tissue-specific endothelial cell position markers or ligands of the present invention (the 58–69 kD proteins, of which the MECA-367/-89, and MECA-79 antigens represent the mucosal and peripheral lymph node prototypes). Thus, this immunologic approach to defining tissue-specific endothelial cell surface molecules present in other sources of endothelial cells has a corollary in studies concerned with the isolation of lymphocyte cell surface molecules. Identification of additional family members of tissue-specific endothelial cell glycoproteins, such as tissue-specific endothelial ligands in synovium, skin, heart and other tissues, will be straightforward based on the disclosure and methods of the present invention.

The ability to inhibit immune system functions is known to be therapeutically useful in treating diseases such as allergies, autoimmune disease including rheumatoid arthritis and systemic lupus erythematosis, certain types of kidney diseases, inflammatory lung diseases such as idiopathic pulmonary fibrosis and hypersensitivity pneumonitis, certain types of endocrinological diseases such as Grave's disease or early diabetes, and certain types of cardiac disease such as rheumatic fever. Immunosuppression is also therapeutically useful in preventing the harmful immune "rejection" response which occurs with organ transplantation or in transplantation of bone marrow cells used to treat certain leukemias or aplastic anemias. According to the invention, tissue-specific immunosuppressive therapies for these and other types of diseases are provided. Some of these diseases are listed below in Table 1.

TABLE 1: EXAMPLES OF DISEASES OR IMMUNOLOGICAL DISORDERS

Autoimmune and Related Disorders

Systemic Lupus Erythematosus
Rheumatoid Arthritis
Polyarteritis Nodosa
Polymyositis and Dermatomyositis
Progressive Systemic Sclerosis (Diffuse Scleroderma)
Glomerulonephritis
Myasthenia Gravis
Sjogren's Syndrome
Hashimoto's Disease and Graves' Disease
Adrenalitis, Hypoparathyroidism, and Associated Diseases
Pernicious Anemia
Diabetes
Multiple Sclerosis and Related Demyelinating Diseaess
Uveitis
Pemphigus and Pemphigoid
Cirrhosis and Other Diseases of the Liver
Ulcerative Colitis
Myocarditis Local Manifestations of Drug Reactions (dermatitis, etc.)

Inflammation-associated or Allergic Reaction Patterns of the Skin
Atopic Dermatitis and Infantile Eczema
Contact Dermatitis
Psoriasis
Lichen planus Allergic enteropathies The Atopic Diseases
Allergic Rhinitis
Bronchial Asthma Transplant Rejection (heart, kidney, lung, liver, pancreatic islet cell, others)

Hypersensitivity or Destructive Responses to Infectious Agents
Poststreptococcal Diseases (e.g. Cardiac manifestations of rheumatic fever)
Others Another aspect of the invention is the targeting of therapeutic or diagnostic reagents (radiotoxins, reagents capable of inducing vascular permeability to enhance access of soluble blood-borne macromolecular reagents to surrounding tissues or neoplasms, or radiologic, nuclear magnetic resonance or other imaging reagents) to specific tissues or organs. Reagents are covalently linked, using conventional techniques, to antibodies to tissue-specific endothelial cell ligands or molecules, and injected intravenously to localize along the vasculature in the target organ or tissue. Such targeting allows novel imaging approaches to the diagnosis of vascular abnormalities or to the evaluation of the vascularization of malignancies. For example, since tissue-specific endothelial cell ligands may be induced inappropriately by factors produced locally by metastatic cells (for instance, mammary gland tissue induces mucosal endothelial ligands locally, and metastatic breast carcinoma might therefore induce mucosa-specific endothelial molecules as well) imaging reagents injected intravenously might readily identify sites of metastatic breast carcinoma. This approach to imaging of neoplasms, based on changes in the surface of endothelial cells in the local vasculature, avoids the problem of delivery of macromolecules to extravascular sites. The invention also permits localized targeted delivery of therapeutic agents to selective tissues or organs.

All inflammatory and immune responses in tissues require absolutely the presence of leukocytes at the site(s) of inflammation. The leukocytes include lymphocytes and their progeny, monocytes, neutrophils, eosinophils, basophils, natural killer cells, and/or mast cells. All such leukocytes originate in the bone marrow, travel through the blood, and only enter tissue sites where they can contribute to immune responses by interacting with and migrating between blood vessel endothelial cells. The ability to prevent leukocyte extravasation into particular organs or tissues therefore provides an effective but tissue-selective immunosuppressive therapy. The present invention permits the targeted inhibition of lymphocyte and leukocyte entry into mucosal lymphoid and inflammatory tissues, into lymph nodes, into synovium and skin, and by extension into other discrete organs such as brain, heart, kidney, lung and liver. The method of the invention therefore provides a preferable mode of immunosuppressive therapy for localized diseases in which inflammatory or immune reactions contribute to pathology.

The antibodies used in the method of the present invention are preferably administered to individuals, preferably mammals, in a manner that will maximize the likelihood of the antibody reaching the targeted endothelial cell, binding to it, and thereby blocking the binding of circulating lymphocytes. This in turn will inhibit or divert lymphocyte traffic through particular sites and thus control certain neoplastic or dysfunctional lymphoid diseases, such as those identified in Table 1.

The dose for individuals of different species and for different diseases is determined by measuring the effect of the antibody on the lessening of those parameters which are indicative of the disease being treated. Being proteins, the antibodies will normally be administered parenterally, preferably intravenously. In a mouse model for local inflammatory disease (e.g., intestinal hypersensitivity response), a dose of MECA-367 antibody of 0.5–2 mg/host/week for 2 (weeks) would be sufficient to reduce inflammation of the disease. The dose of the antibody may have to be repeated periodically depending on the particular disease. Moreover, the effects of many autoimmune diseases are considered irreversible, e.g., the collagenization in sarcoidosis, or the terminal effects of prolonged rheumatoid arthritis. Thus, treatment of the susceptible individual will be prior to terminal manifestation of the disease, and possibly prior to the onset of the disease. Whether or not a disease is fully manifested may be determined by monitoring clinical symptoms, as well as the presence of specific antibodies associated with the autoimmune disease.

When administered parenterally the antibodies will be formulated in an injectable dosage form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and Hanks' solution. Nonaqueous vehicles such as fixed oils and ethyl oleate may also be used. The vehicle may contain minor amounts of additives such as substances that enhance isotonicity and chemical stability, e.g., buffers and preservatives. The antibody is preferably formulated in purified form substantially free of aggregates and other proteins at concentrations of about 1 to 50 mg/ml.

For arthritis, local administration may be particularly effective, using means of subcutaneous implant, staples or slow release formulation implanted directly proximal the target. Slow-release forms can be formulated in polymers, such as Hydron (Langer, R., et al (1976) *Nature* 263:797–799) or Elvax 40P (Dupont) (Murray, J. B., et al. (1983) *In Vitro* 19:743–747). Other sustained-release systems have been suggested by Hsieh, D. S. T., et al. (1983) *J Pharm Sci* 72:17–22). Suitable pharmaceutical vehicles and their formulations are described in "Remington's Pharmaceutical Sciences" by E. W. Martin which is incorporated herein by reference.

The following examples further illustrate the invention. These examples are not intended to limit the scope of the invention. In light of the present disclosure, numerous embodiments within the scope of the claims will be apparent to those of ordinary skill in the art.

EXAMPLES

Antigen Source

From functional studies of lymphocyte-endothelial cell interactions in vivo and in vitro, it has been shown that lymph node HEV are specialized in their expression of functionally defined tissue-specific ligands for lymphocyte homing receptors. Furthermore, the HEV in mesenteric lymph nodes are known to bind both lymph node-specific and mucosal HEV-specific cell lines. Thus, in order to produce antibodies against peripheral lymph node-specific and mucosal lymphoid-specific endothelial cell ligands, a crude pooled preparation containing high endothelial venules from peripheral and mesenteric lymph nodes was used.

Brachial, axillary, inguinal, and mesenteric lymph nodes from BALB/c mice were pooled in Hank's balanced salt solution (HBSS), minced, and gently pressed between glass microscope slides to release lymphocytes. The resulting cell suspension was then passed through nitex mesh (Sullivan's, San Francisco, Calif.), and the stromal elements which remained on top of the mesh were collected. These stromal preparations were treated for 10 minutes with HBSS containing 0.32 mg collagenase/ml (5 ml/mouse), washed, and again passed through nitex. The stromal cells remaining on the nitex were collected, suspended in HBSS, and used for immunization.

Immunization Protocols

For the fusion which led to the generation of MECA-89, a Wistar rat received three intraperitoneal (i.p.) priming doses of lymph node stroma (from 3 mice/injection) mixed with precipitated aluminum potassium sulfate (adjuvant/carrier) in a 3:2 ratio, final volume 1 ml. These immunizations were given two to three weeks apart, and 17 days after the third priming dose, the rat was boosted i.p. with stromal cells (from 10 mice) in HBSS.

For the fusion which led to the generation of MECA-367 (ATCC NO. HB9478) and MECA-79, (ATCC NO. HB9479) approximately $1 \times 10^8$ spleen cells from the animal used for the MECA-89 fusion were adoptively transferred to a normal Wistar rat. On the day following cell transfer, and again two months later, this animal was immunized with lymph node stroma (from 5 mice/injection) mixed with precipitated aluminum potassium sulfate. One week after this second immunization, the rat was boosted i.p. with a stromal cell preparation (from 10 mice) in HBSS.

Hybridoma Production

Three (MECA-89 fusion) to four (MECA-367/MECA-79 fusion) days after final boosts, rat spleen cells were mixed with the mouse myeloma Sp2/O (ATCC HB American Type Culture Collection, Rockville, Md.), at a lymphocyte to myeloma ratio of two to one, and fused using polyethylene glycol 4000, gas chromatography grade (EM Science, West Germany). Hybrid cells were selected for their ability to grow in RPMI 1640 medium (JR Scientific) containing hypoxanthine, aminopterin, and thymidine (Kohler and Milstein, Nature, supra).

Monoclonal Antibody Screening

Screening of Monoclonal Antibodies was Carried out as Follows

1. Initial immunohistologic selection by immunofluorescence: Hybridoma supernatants were screened for the presence of monoclonal antibodies recognizing endothelial cells, in particular lymphoid tissues and inflammatory sites. Lymphoid and in some cases extralymphoid tissues were embedded in Tissue Tek OCT compound (Lab-Tek Products) and frozen on dry ice. 8–12 um thick frozen sections were cut and fixed by 2 to 10 minute immersion in cold acetone, and allowed to air dry. The sections were covered with 50–100 ul of hybridoma supernatant, incubated 10 minutes, and washed by immersion $\times 5$ minutes in HBSS. Slides were then incubated for 10 minutes at room temperature in Coplin jars containing a 1:20 dilution of second-stage antibody, FITC-conjugated goat anti-rat IgG (Sigma) in HBSS containing 5% normal mouse serum. Slides were washed in HBSS, and examined by fluorescence microscopy. Supernatants containing antibodies reactive with high endothelial venules cells in lymph nodes and/or in Peyer's patches, were selected for cloning by limiting dilution.

Additional immunohistologic staining was carried out by immunoperoxidase staining. Acetone-fixed frozen sections (6–12 um thick) of various lymphoid and extralymphoid tissues were incubated with purified monoclonal antibody in phosphate buffered saline (PBS), washed, and treated with a solution of horseradish peroxidase conjugated rabbit anti-rat IgG (DAKO, Copenhagen, Denmark; used at 1:40), 5% normal mouse serum, and PBS. The horseradish peroxidase conjugated second antibody was detected following exposure to a solution of diaminobenzidine and $H_2O_2$, and the staining was enhanced by incubation in 0.5% copper sulfate in saline. Sections were lightly counterstained with hematoxylin.

Hybridomas producing antibodies that stained HEV in a tissue-selective manner were subcloned by limiting dilution, and stable clones were frozen in liquid nitrogen for storage. These included MECA-89 and MECA-367, specific for HEV in mucosa-associated tissues; and MECA-79, which preferentially stains lymph node HEV and recognizes Peyer's patch HEV only weakly or focally.

Aliquots of the subcloned hybridomas were adapted for growth in HB101 serum free medium (New England Nuclear) and grown in bulk for production of monoclonal antibodies. Immunoglobin in the resulting culture supernatant were precipitated by addition of ammonium sulfate to 50% saturation, and the yield and purity of monoclonal antibodies was determined by protein measurement ($OD_{280}$) and SDS-PAGE analysis.

2. Functional assay of ability of antibodies to block lymphocyte-endothelial cell recognition in an in vitro lymphocyte-endothelial cell binding assay: The in vitro model of the interaction between lymphocytes and HEV has been previously described (Butcher, et al., J Immunol, supra and Jalkanen and Butcher, Blood, supra), but was slightly modified in this investigation to allow assessment of the blocking activity of MECA-89, MECA-367, and MECA-79. Briefly, the antibodies defining the HEV of mucosal or peripheral lymphoid tissues were preincubated on 12 um thick, freshly cut, unfixed frozen sections of lymph nodes or Peyer's patches for 30 minutes at 7° C. Controls included an isotype-matched monoclonal antibody and medium alone. Antibodies were used at a concentration of 100 ug/ml, and 100 ul were applied to each section. Following this preincubation, the medium was removed from both experimental and control sections, and the lymphocyte-HEV binding assay was conducted. For the binding assay, mouse mesenteric node lymphocytes or selected lymphoid lines or lymphomas in RPMI 1640 containing 20 mM HEPES and 5% newborn or fetal calf serum were studied.

a. Standard assay conditions were: One hundred ul of a suspension of lymphocytes at $3 \times 10^7$ per ml in cell suspension medium (RPMI containing 25 mM/L HEPES, pH 7.3, and 5.0% fetal calf serum) were incubated in 12 um fresh-frozen sections of three human lymph nodes in a wax pen circle (Martex, Tech Pen, Scientific Products, McGraw Park, Ill.) 1.8 cm in internal diameter. Clumps were removed from the sample populations prior to assay by passing the cell suspension through monofilament nylon mesh (Sullivans, San Francisco, Calif.). The sections were rotated on a Tekpro-t (American Scientific Products, Sunnyvale, Calif.) shaker at 60–70 rpm for 30 minutes at 7° C. ($\frac{3}{4}''$ radius of rotation, horizontal motion). It is important to begin agitation prior to addition of sample cells. After incubation, the medium was removed by gently rapping the edge of the slide against an absorbent towel. Slides were then placed on edge in 1% glutaraldehyde (diluted from 49% stock, MCB, Manufacturing Chemists, Cincinnati, Ohio) in cold PBS and left overnight to fix adherent lymphocytes to the section.

b. Identification and counting of HEV-adherent lymphocytes: After incubation and fixation, nonadherent lymphocytes were rinsed off with a gentle stream of PBS, and the sections were examined with a 16x objective by darkfield illumination under PBS. Under these conditions, HEVs can be clearly distinguished from surrounding paracortex by a distinct dark line (the basement membrane) that delineates their characteristic round to elongated shape. Adherent lymphocytes appear as distinct bright circles lying above the plane of the tissue section. The number of lymphocytes bound to each HEV was recorded. For most experiments, six sections per sample were coded and counted single-blind. Areas with heavy nonspecific binding were not counted.

c. Data treatment: The mean number of cells bound to the individually scored HEVs and the standard error of the mean were calculated for each sample.

As shown in Table 2, MECA-79 inhibits the binding of lymphocytes to peripheral lymph node HEV by 95%, without effecting binding to HEV in the gut-associated Peyer's patches. Conversely, MECA-367 inhibits binding to Peyer's patch HEV by 90%, without influencing adherence to lymph node HEV. Control antibodies as well as MECA-89 were without significant effect. MECA-79 and -367 also block (with the same specificity) the binding of transformed lymphoid cell lines. Thus MECA-79 and MECA-367 inhibit tissue-specific lymphocyte endothelial cell interactions required for extravasation from the blood into peripheral lymph nodes or into mucosal Peyer's patches, respectively.

TABLE 2

ORGAN-SPECIFIC INHIBITION OF LYMPHOCYTE-HEV BINDING BY MONOCLONAL ANTIBODIES MECA-367 AND MECA-79

| TISSUE | ANTIBODY TREATMENT | CELLS/HEV ($\bar{x} \pm$ SE) | BINDING AS % OF CONTROL |
| --- | --- | --- | --- |
| Peyer's patches | Medium Control | 1.14 ± 0.06 | (100) |
| | MECA-367 | 0.11 ± 0.04 | 10* |
| | MECA-89 | 1.00 ± 0.17 | 88 |
| | IgG2a control | 1.01 ± 0.12 | 89 |
| | MECA-79 | 1.09 ± 0.16 | 96 |
| | IgM control | 1.18 ± 0.17 | 104 |
| Peripheral lymph nodes | Medium Control | 14.5 ± 1.4 | (100) |
| | MECA-367 | 15.9 ± 1.4 | 110 |
| | MECA-89 | 16.3 ± 1.6 | 112 |
| | IgG2a control | 14.0 ± 1.7 | 92 |
| | MECA-79 | 0.77 ± 0.2 | 5* |
| | IgM control | 13.8 ± 1.5 | 95 |

*$P < 0.001$ vs. other treatments

Antibodies capable of blocking lymphocyte HEV interaction in the in vitro assay were selected for subsequent in vivo studies. In addition, antibodies recognizing tissue-specific or inflammation-specific determinants on endothelial cells, whether or not they exhibited inhibition in the in vitro assay, were also selected for inhibition for in vivo studies when deemed appropriate. (For example, MECA-89 fails to inhibit lymphocyte-HEV interactions in vitro, yet blocks lymphocyte homing to mucosal Peyer's patches by 80% in vivo—see below. This antibody has been shown to bind the same mucosal endothelial cell molecule defined by the completely blocking antibody, MECA-367.)

3. Inhibition of in vivo homing:

a. In vitro labeling of normal lymphocytes with $^{51}$Cr: Normal mesenteric node lymphocytes were recovered from minced nodes that were gently pressed through metal gauze under frequent flushing with HBSS. Lymphocytes were washed, and labeled at $1 \times 10^7$ cells/ml using a modification of a standard technique (Butcher and Ford, Chapter 57, in *Handbook of Experimental Immunology*, Vol. 2, Weir and Herzenberg, Eds. 1986, 4th Edition, Blackwell Publishers). Briefly, cells were incubated with 100 Ci/ml sodium chromate (Na$_2$ $^{51}$CrO$_4$, New England Nuclear, Boston, Mass.) for 1 hour, with mixing every 10–15 minutes at 37° C. in DMEM (Gibco) supplemented with 20 mM HEPES and 5% FCS. After labeling, the cells were centrifuged through a layer of FCS, and washed twice with HBSS prior to injection into animals.

b. In vivo homing: For the assessment of antibody blocking activity, mice received tail vein injections of either HBSS alone, MECA-367, MECA-89, MECA-79, or IgG2a control antibody Hermes-1 (1 mg doses were given). In some experiments, mice received two antibody injections, the first being one day before the assay, and the second, 4 hours before injection of labeled cells. In most experiments, mice received one antibody injection 4 hours before administration of labeled cells. $2 \times 10^7$ labeled cells bearing 385,000 cpm $^{51}$Cr were delivered in vivo by tail vein injection, and 1 hour after the administration of cells, animals were euthanized, various organs were harvested, and lymphocyte localization into the various tissues were determined by quantitating the $^{51}$Cr in each organ on a Packard gamma counter.

The results are presented in Table 3. MECA-367 and MECA-89 selectively inhibit lymphocyte extravasation into mucosal Peyer's patches, and MECA-79 inhibits lymphocyte localization to peripheral lymph nodes.

TABLE 3

In Vivo Blockade of Homing Organ

| Antibody Treatment | Peripheral Lymph Node* | Mucosal Peyer's Patches | Spleen |
|---|---|---|---|
| Media Control | 11,500 ± 3545**cpm | 5468 ± 477 | 117,579 ± 16,179 |
| MECA-367 | 10,224 ± 1041 cpm (89)*** | 181 ± 36 (3) | 122,940 ± 16,543 (104) |
| MECA-89 | 11,107 ± 370 (97) | 1114 ± 98 (20) | 109,598 ± 9521 (93) |
| MECA-79 | 5743 ± 524 (50) | 5028 ± 1669 (92) | 139,709 ± 12,894 (119) |

*axillary, brachial, inguinal
**mean ± SE of cpm localized in organ 1 hour after injection of labeled lymphocytes
***localization as percent of control cells

Identification of Endothelial Cell Antigen Defined by Antibodies MECA-367 and MECA-89

Mesenteric nodes from ten 12-week old Balb/c mice were minced and most lymphocytes were flushed away from stromal tissue by flushing with HBSS over a wire mesh. The crude stromal preparation was suspended in 30 ml and stromal tissue allowed to settle to further separate stroma from lymphocytes. The stromal preparation was washed once with HBSS and pelleted by centrifugation at 250 g for 7 minutes. The crude stromal isolate was lysed by addition of 10 ml of Tris lysis buffer (TLB; 2% NP-40, 150 mM sodium chloride, 1 mM $MgCl_2$, 0.02% $NAN_3$, and 1% aprotinin, 1% leupeptin, 1% pepstatin, 1 mM PMSF, and 20 mM Tris-HCl pH 8.0), and incubated 90 minutes on ice. The lysate was then clarified by centrifugation for 15 minutes at 100,000 g.

Affinity columns were produced by conjugating MECA-367 antibody or control rat IgG2a (Hermes-1, of irrelevant specificity) antibody at 1.5 mg antibodies/ml packed beads to CNBr-activated Sepharose 4B beads per the manufacturers directions (Pharmacia, Sweden). The clarified lymph node stromal lysate was sequentially applied to 1 ml control antibody and 1 ml specific MECA-367 antibody columns at room temperature and 1 ml/minute. Both columns were washed extensively in wash buffer (0.1% NP-40, 500 mM NaCl, 50 mM Tris-HCl pH 7.4, 1% leupeptin, 1% pepstatin, 1% aprotinin, and 1 mM PMSF) and separately eluted with 0.2M acetic acid, 500 mM sodium chloride, 0.1% NP-40 solution. Ten fractions of 600 ul were collected, the pH was measured by standard pH paper and 1M Tris-HCl, pH 8.0 was added to neutralize each fraction. Fractions 2-5 were pooled and concentrated by centrifugation with Centricon 10 microconcentrators (Amicon) to 200 ul. The eluate from the MECA-367 antibody column but not the control column contained the mucosa-specific endothelial determinant, as demonstrated by immunoblot analyses. Briefly, 2 ul of the concentrated eluates were applied to nitrocellulose paper (Bio-Rad Transplot) and allowed to dry. The nitrocellulose was blocked by incubation with 10% horse serum in TBST (10 mM Tris-HCl pH 7.4, 150 mM NaCl, 0.5% Tween-20) for 30 minutes at room temperature. The nitrocellulose blots were then incubated at room temperature for 30 minutes with 100 ug/ml MECA-367 in TBST (or with control antibody Hermes-1), washed 3 times for 10 minutes each in TBST at room temperature, and incubated in second-stage indicator antibody, alkaline phosphatase-conjugated goat anti-rat IgG (Sigma, Catalog# A-9645) at 1:200 for 30 minutes at room temperature with gentle shaking. The blots were washed 3 times as above and were developed by addition of AP substrate solution (100 mM Tris-HCl pH 9.5, 100 mM sodium chloride, 5 mM $MgCl_2$ containing 33 ul NBT (nitro blue tetrazolium, 50 mg/ml 70% dimethyl formamide) and 16.5 ul BCIP (5-bromo-4-chloro-3-indolyl phosphate, 50 mg/ml dimethyl formamide) per 5 ml solution). The reaction was terminated after 30 minutes by addition of 20 mM Tris-HCl, pH 7.4 and 5 mM EDTA. The eluate of the MECA-367 column, but not the control column contained material immunoreactive with MECA-367. This specific eluate also reacted with MECA-89, demonstrating that the MECA-367 antigen also bears the MECA-89 epitope- The control antibody Hermes-1 gave no signal in the immunoblot analyses of control or specific antibody column eluates.

Western analyses, using sodium dodecyl sulfate/polyacrylamide gel electrophoresis (SDS-PAGE) and immunoblotting analysis were carried out to identify the molecular weight of the MECA-367 antigen. Fifty ul of the concentrated eluates from the control or specific antibody columns were mixed with an equal volume of Laemmli sample buffer (Laemmli, 1970, Nature 227:680) and applied to a 8% SDS-PAGE gel and electrophoresed under reducing conditions. The gel contents were then transferred electrophoretically to nitrocellulose (by electroblotting using a Bio-Rad Transblot apparatus in the presence of a glycine/methanol buffer as described by the manufacturer). The antigen was detected by immunologic analysis as described above for immunoblot analysis: first-stage antibody (MECA-367, or in control gel transfers, Hermes-1) was incubated with nitrocellulose blots at 100 ug/ml in 20 ml TBST at room temperature for 30 minutes. The filters were washed, exposed to second-stage antibody, and developed by the addition of AP substrate solution (see above). The procedure revealed the MECA-367 antigen to be a molecule of approximately 58–69 kD apparent molecular weight under these conditions of electrophoresis. MECA-89 reacted with the same band, confirming that the MECA-89 and MECA-367 epitopes are on the same mucosa-specific endothelial cell molecule.

Production of Antibodies Against Human Endothelial Cells Involved in Lymphocyte Traffic The same techniques are applicable to the production of antibodies to human endothelial cells involved in lymphocyte traffic. Two examples illustrate this point: First, monoclonal antibody MECA-79, described above and originally isolated as defining mouse lymph node high endothelial molecules for lymphocyte binding, has been found to cross-react antigenically and functionally (by binding to lymph node HEV and blocking lymphocyte binding to HEV) with human HEV. Secondly, a monoclonal antibody specific for human HEV, HECA-452, has been produced by immunizing rats with crude stromal preparations of human tonsils, using procedures paralleling those described in the foregoing examples.

Production of Monoclonal Antibody HECA-452, Specific for Human HEV

As a source for lymphoid tissue rich in HEV, tonsillectomy specimens were obtained through the Department of Pathology, Stanford University Medical Center. Fresh or stored frozen tissues were trimmed into pieces of about 0.5 cm³ and were squeezed on metal gauze under frequent flushing with RPMI 1640 medium (from Gibco; containing 20 mM HEPES, pH 7.3) to remove lymphocytes. Stromal remnants left on top of the screen were collected, and were homogenized in PBS in a ground glass homogenizer routinely used for preparing cell suspensions from lymphoid organs. The homogenate was centrifuged (200 xg, 10 minutes at 4° C.) and the pellet thoroughly mixed with Freund's adjuvant in a 1:1 ratio (final volume 1 ml), and used for immunization.

Three-to-four month old Wistar rats were immunized with 1 ml of the stromal preparation of tonsil (0.5 cm³/rat) in complete Freund's adjuvant intraperitoneally. About 3-4 weeks later the rats were boosted i.p. with a stromal preparation of tonsil in incomplete Freund's adjuvant.

Four days after boosting, rat spleen cells were fused with Sp2/0 mouse myeloma cells as above. Supernatants were screened for reactivity with HEV in frozen sections of human tonsil tissue by the immunoperoxidase technique described above. The hybridoma producing the HECA-452 antibody was subcloned by limiting dilution and expanded.

In immunoperoxidase staining of sections of lymphoid organs the HECA-452 antibody clearly stained all HEV observed in tonsils, lymph nodes, and gut-associated lymphoid tissue (GALT). The antibody was highly selective for the endothelium of HEV, staining the high endothelium intensely. In most studies, no other vessels were stained. In occasional hyperplastic tonsils, however, weak reactivity was observed with small venules around the periphery of organized lymphoid accumulations. The antibody exhibited no reactivity with the endothelium of capillaries, arterioles, or larger veins in lymphoid tissues, and failed to stain any vessel in thymus and spleen, lymphoid organs lacking functional HEV.

In addition to high endothelium, HECA-452 also stained a small population of cells scattered primarily within the T cell areas in lymphoid organs and also in the red pulp of the spleen. These cells were more or less round, mononuclear with an eccentric nucleus, and larger than most lymphocytes. Double staining of sections immunohistologically with HECA-452 and histochemically with acid phosphatase demonstrated that these cells are weakly acid phosphatase positive. From these data it is most likely that the cells belong to the lineage of monocytic cells.

HECA-452+ vessels were absent in sections of numerous normal non-lymphoid tissue specimens, except in the setting of dense infiltration by chronic inflammatory cells, especially lymphocytes.

UTILITY

The utility of the invention is in the control of inflammatory and immune responses in tissues or organs of the body. In particular, the utility of the present invention is in the ability to inhibit inflammatory and immune responses selectively in particular target organs by specifically interfering with leukocyte entry into the target organ. The invention avoids the non-specific generalized suppression of immune responses currently induced by immunosuppressive therapeutic regimens, and therefore offers a preferred mode of treatment for localized diseases in which immune and inflammatory reactivities contribute to pathology.

The following cell lines were deposited with the American Type Culture Collection, Rockville, Md., 20852 (ATCC). These deposits were made under the provisions of the Budapest Treaty on the International Recognition of the Deposit of Microorganisms for purposes of Patent Procedure and the Regulations thereunder (Budapest Treaty). This assures maintenance of a viable culture for 30 years from the date of deposit. The cell lines will be made available by ATCC under the terms of the Budapest Treaty, and subject to an agreement between applicant and ATCC that assures unrestricted availability upon issuance of the pertinent U.S. patent. Availability of the deposited cell lines is not to be construed as a license to practice the invention in contravention of the rights granted under the authority of any government in accordance with its patent laws.

| Cell Line | ATCC No. | Deposit Date |
|---|---|---|
| MECA 367 | HB9478 | 10 July 1987 |
| MECA 79 | HB9479 | 10 July 1987 |

The foregoing written specification is considered to be sufficient to enable one skilled in the art to practice the invention. The present invention is not to be limited in scope by the cell lines deposited, since the deposited embodiments are intended as illustrations of the invention. The deposit of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention would be appreciated by those skilled in the art from the foregoing description and fall within the scope of the appended claims.

I claim:

1. A monoclonal antibody selected from the group consisting of MECA-367, MECA-379, a monoclonal antibody that binds to the same antigan as MECA-367, and a monoclonal antibody which binds to the same antigen as MECA-79, wherein said antibody inhibits leukocyte-endothelial cell adhesion by binding to a tissue specific endothelial cell surface antigen and blocks the leukocyte homing receptor endothelial cell surface antigen interaction.

2. An antibody fragment of an antibody selected from the group consisting of MECA-367, MECA-79, a monoclonal antibody that binds to the same antigen as MECA-367, and a monoclonal antibody which binds to the same antigen as MECA-79, wherein said antibody fragment inhibits leukocyte-endothelial cell adhesion by binding to a tissue specific endothelial cell surface antigen and blocks the leukocyte homing receptor-endothelial cell surface antigen interaction.

3. A monoclonal antibody or antibody fragment of either claim 1 or 2, wherein said leukocytes are lymphocytes.

4. A monoclonal antibody according to claim 1, wherein said monoclonal antibody is MECA-367 or a monoclonal antibody which binds to the same antigen as MECA-367 and blocks leukocyte-endothelial cell adhesion.

5. A monoclonal antibody according to either claim 1 or 4, wherein said monoclonal antibody is produced by the hybridoma having ATCC Accession Number HB9478.

6. A monoclonal antibody according to claim 1, wherein said monoclonal antibody is MECA-79 or a monoclonal antibody which binds to the same antigen as MECA-79 and blocks leukocyte-endothelial cell adhesion.

7. A monoclonal antibody according to either claim 1 or 6, wherein said monoclonal antibody is produced by the hybridoma having ATCC Accession Number HB9479.

* * * * *